(12) United States Patent
Baldasaro et al.

(10) Patent No.: US 12,345,397 B2
(45) Date of Patent: Jul. 1, 2025

(54) MULTI-LAMP LIGHTING SYSTEM

(71) Applicant: Al Errington, Batchawana Bay (CA)

(72) Inventors: Anthony Baldasaro, Kitchener (CA); Apoorva Dilip Yadav, Maharashtra (IN); Al Errington, Kitchener (CA)

(73) Assignee: Al Errington (CA)

( * ) Notice: Subject to any disclaimer, the term of this patent is extended or adjusted under 35 U.S.C. 154(b) by 0 days.

(21) Appl. No.: 17/535,044

(22) Filed: Nov. 24, 2021

(65) Prior Publication Data

US 2022/0163194 A1     May 26, 2022

Related U.S. Application Data

(60) Provisional application No. 63/118,427, filed on Nov. 25, 2020.

(51) Int. Cl.
| | |
|---|---|
| *F21V 23/04* | (2006.01) |
| *A61L 2/00* | (2006.01) |
| *A61L 2/24* | (2006.01) |
| *F21Y 113/10* | (2016.01) |

(52) U.S. Cl.
CPC ........ *F21V 23/0471* (2013.01); *A61L 2/0047* (2013.01); *A61L 2/24* (2013.01); *A61L 2202/11* (2013.01); *A61L 2202/14* (2013.01); *F21Y 2113/10* (2016.08)

(58) Field of Classification Search
CPC ..... A61L 9/20; A61L 2/20; A61L 2/24; A61L 2202/14; A61L 2209/12; A61L 2202/11; A61N 2005/0652; A61N 2005/0626; A61N 2005/0636; A61N 2005/0662
See application file for complete search history.

(56) References Cited

U.S. PATENT DOCUMENTS

| | | | |
|---|---|---|---|
| 2009/0117000 A1 | 5/2009 | First et al. | |
| 2020/0289698 A1 | 9/2020 | Polidoro | |
| 2021/0113723 A1* | 4/2021 | Malinowski | A61L 2/10 |
| 2022/0072186 A1* | 3/2022 | Maa | A61L 2/20 |

FOREIGN PATENT DOCUMENTS

| | | |
|---|---|---|
| BR | 102018068501 A2 | 12/2018 |
| KR | 101680488 B1 * | 11/2016 |
| TR | 202007505 A2 | 6/2020 |

OTHER PUBLICATIONS

International Search Report and Written Opinion, Canadian Intellectual Property Office (Mar. 4, 2022).

(Continued)

*Primary Examiner* — Elmito Breval
(74) *Attorney, Agent, or Firm* — Valauskas Corder LLC

(57) ABSTRACT

A lighting system, including a sensor operable to detect a person, a luminaire, and a tracking system. The luminaire including a first lamp operable to generate visible light when activated, and a second lamp operable to generate UVC light having a peak wavelength between 200 nm and 225 nm when activated, the second lamp communicatively coupled to the sensor and configured to be activated in response to the sensor detecting the person. The tracking system operable to track how long the second lamp has been activated and generate to-date usage information, the to-date usage information indicating a total amount of time the second lamp has been activated so far.

20 Claims, 5 Drawing Sheets

(56) References Cited

OTHER PUBLICATIONS

Genpro Advanced Technologies, "UVC Sterilization Troffer", 5 pages, Jul. 31, 2020.
Simons, R. M et al., "Far UV-C in the 200-225 nm range, and its potential for disinfection applications", International Ultraviolet Association, 11 pages, Jul. 2020.
Ashdown, I., Designing a UV-C Germicidal System, Illuminating Engineering Society, May 29, 2020.
FDA, "UV Lights and Lamps: Ultraviolet-C Radiation, Disinfection, and Coronavirus", Content current as of: Feb. 1, 2021.
Hessling, M. et al., "The impact offar-UVC radiation (200—230 nm) on pathogens, cells, skin, and eyes—a collection and analysis of a hundred years of data", GMS Hygiene and Infection Control 2021, vol. 16, 17 pages, Feb. 16, 2021, ISSN 2196-5226, doi: 10.3205/dgkh000378.
Buonanno, M. et al., "Far-UVC light (222 nm) efficiently and safely inactivates airborne human coronaviruses", Scientific Reports, 2020, 10: 10285.

\* cited by examiner

MULTI-LAMP LIGHTING SYSTEM

CROSS REFERENCE TO RELATED APPLICATIONS

This application claims the benefit of U.S. Provisional Patent Application No. 63/118,427 filed Nov. 25, 2020, the contents of which are hereby incorporated by reference.

FIELD

The specification relates generally to apparatuses and methods associated with lighting systems, and more specifically to a multi-lamp lighting system.

BACKGROUND

It has long been known that some ultraviolet (UV) radiation is effective in killing pathogens. In particular, UVC radiation (200 nm to 280 nm in wavelength) is effective in killing pathogens.

UVC radiation has been used as a germicidal light in many applications. Often, radiation having a peak wavelength of ~254 nm is used, as this radiation has been shown to be effective.

Buonanno et al. (Far-UVC light (222 nm) efficiently and safely inactivates airborne human coronaviruses. Sci Rep 10, 10285 (2020). https://doi.org/10.1038/s41598-020-67211-2) purport to disclose that far-UVC light (207-222 nm) efficiently kills pathogens potentially without harm to exposed human tissues. Buonanno et al. suggest that continuous far-UVC (207-222 nm) exposure in occupied public locations at the current regulatory exposure limit (~3 mJ/cm2/hour) would result in ~90% viral inactivation in ~8 minutes, 95% in ~11 minutes, 99% in ~16 minutes and 99.9% inactivation in ~25 minutes. Buonanno et al. suggest that, while staying within current regulatory dose limits, low-dose-rate far-UVC exposure can provide a major reduction in the ambient level of airborne coronaviruses in occupied public locations.

SUMMARY

The following summary is intended to introduce the reader to various aspects of the applicant's teaching, but not to define any invention.

According to some aspects, there is provided a lighting system, comprising a sensor operable to detect a person; a luminaire, including: a first lamp operable to generate visible light when activated, and a second lamp operable to generate UVC light having a peak wavelength between 200 nm and 225 nm when activated, and wherein the second lamp is communicatively coupled to the sensor and configured to be activated in response to the sensor detecting the person; a tracking system operable to track how long the second lamp has been activated and generate to-date usage information, the to-date usage information indicating a total amount of time the second lamp has been activated so far.

In some examples, the sensor is operable to detect the person when the person is within an activation range of the second lamp, and the second lamp is configured to be activated in response to the sensor detecting the person when the person is within the activation range.

In some examples, the activation range is an effective range of the UVC light of the second lamp, and the peak wavelength of the UVC light generated by the second lamp when the second lamp is activated is between 221 nm and 223 nm.

In some examples, the second lamp is configured to remain activated for a predetermined activation time after the sensor detects the person when the person is within the activation range, and the second lamp is configured to deactivate after the predetermined activation time.

In some examples, the sensor is supported by the luminaire.

In some examples, the first lamp is configured to be activated when the luminaire is powered by a power source, and the second lamp is configured to be deactivated until both the luminaire is powered by the power source and the sensor detects the person when the person is within the activation range.

In some examples, the first lamp is also configured to be deactivated until both the luminaire is powered by the power source and the sensor detects the person when the person is within the activation range.

In some examples, the first lamp is configured to remain activated as long as the luminaire is powered by the power source regardless of whether the sensor detects the person when the person is within the activation range.

In some examples, the tracking system is further operable to send the to-date usage information to a remote device.

In some examples, the tracking system is configured to send the to-date usage information periodically.

In some examples, the tracking system includes a wireless relay configured to transmit the to-date usage information to a remote device.

In some examples, wireless relay is a Wi-Fi™ relay or a Bluetooth™ relay.

In some examples, the remote device is at least one server.

In some examples, the first lamp is a set of two lamps each operable to generate visible light when activated.

In some examples, the lighting system further comprises a safety system including a UV sensor and operable to shut off the second lamp if the UV sensor detects that the second lamp is emitting light outside of a predetermined safe range.

In some examples, the predetermined safe range is 200 nm to 230 nm.

According to some aspects, there is provided a method of operating a luminaire, comprising (a) providing power to the luminaire from a power source to activate a first lamp of the luminaire, the first lamp generating visible light; (b) detecting, after (a), a person within an activation region adjacent the luminaire; and (c) activating, in response to (b), a previously-deactivated second lamp of the luminaire, the second lamp generating UVC light having a peak wavelength between 200 nm and 230 nm.

In some examples, the method further comprises, following (c), tracking to-date usage information, the to-date usage information indicating a total amount of time the second lamp has been activated so far.

In some examples, the method further comprises activating, in response to (b) a third lamp of the luminaire, the third lamp generating UV light having a peak wavelength between 270 nm and 330 nm.

According to some aspects, there is provided a luminaire, comprising a first lamp for general lighting, the first lamp operable to generate visible light when activated; a second lamp for disinfection, the second lamp operable to generate UVC light having a peak wavelength between 200 nm and 230 nm when activated; and a third lamp for causing vitamin D production, the third lamp operable to generate UV light having a peak wavelength between 270 nm and 300 nm when activated.

BRIEF DESCRIPTION OF THE DRAWINGS

The drawings included herewith are for illustrating various examples of articles, methods, and apparatuses of the present specification and are not intended to limit the scope of what is taught in any way. In the drawings.

DETAILED DESCRIPTION

Various apparatuses or processes will be described below to provide an example of an embodiment of each claimed invention. No embodiment described below limits any claimed invention and any claimed invention may cover processes or apparatuses that differ from those described below. The claimed inventions are not limited to apparatuses or processes having all of the features of any one apparatus or process described below or to features common to multiple or all of the apparatuses or process described below. It is possible that an apparatus or process described below is not an embodiment of any claimed invention. Any invention disclosed in an apparatus or process described below that is not claimed in this document may be the subject matter of another protective instrument, for example, a continuing patent application, and the applicants, inventors or owners do not intend to abandon, disclaim, or dedicate to the public any such invention by its disclosure in this document.

While many types of germicidal radiation are harmful to humans, some types of germicidal radiation are generally safe. Accordingly, in contrast to the usual practice of taking steps to minimize the risk that humans will be exposed to the radiation, systems and methods may be employed which encourage the exposure of humans to the radiation.

Figure 1:
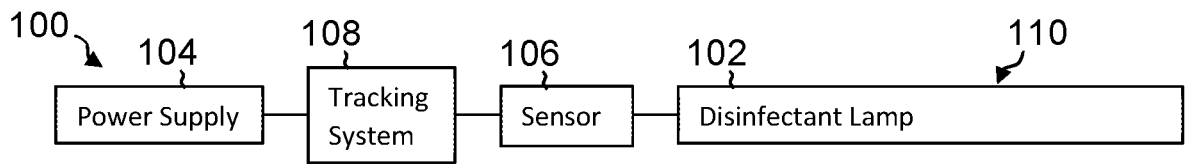
FIG. 1 is schematic diagram of a first example of a lighting system.

Referring to FIG. 1, illustrated is an example of a lighting system 100. The lighting system includes at least one disinfectant lamp 102 operable to generate UVC light when activated.

In some examples, the at least one disinfectant lamp 102 is configured to generate, when activated, light having a peak wavelength that is generally safe for human exposure. For example, the peak wavelength may be between 200 nm and 230 nm, between 206 nm and 223 nm, between 206 nm and 208 nm, between 221 nm and 223 nm, or approximately 222 nm. UVC light at 222 nm may inactivate viruses, such as inactivating more than 95% of airborne aerosolized H1N1 influenza viruses at a low dose of 2 mJ/cm$^2$.

An example of a disinfectant lamp is the SafeGlo2221.5FT by GMY Lighting Technology Co., Ltd., having a peak wavelength of 222 nm and a UV intensity of about 65 $\rho$W/cm$^2$, with a lifespan of about 3,000 hours and configured to be switched off and on more than 10,000 times.

Since the at least one disinfectant lamp 102 is configured to generate light having a peak wavelength that is generally safe for human exposure (e.g. due to light at wavelengths from 207 nm to 222 nm being absorbed by the dead outer layer of skin and by the outer tear layer of the eye), the at least one disinfectant lamp 102 can be safely used near and/or around humans. Accordingly, the lighting system 100 is configured to more directly protect a person by irradiating near and/or around the person (i.e., rather than seeking to disinfect air and/or surfaces prior to exposing the person to the air and/or surfaces), as discussed further below.

The lighting system 100 includes a power supply 104. The power supply 104 is operable to provide power to the at least one disinfectant lamp 102. In some examples, the power supply 104 includes an onboard power source (e.g., a battery, capacitor or fuel cell). Alternatively, or in addition, in some examples the power supply 104 includes a coupling member to be joined to an external pour source (e.g., the coupling member may be an electrical cord and plug to be plugged into a power grid of a facility, such as an electrical outlet in a warehouse).

The lighting system 100 is configured to irradiate a person and/or the air around the person with UVC light to disinfect the person and/or the air around the person. For example, the lighting system 100 may be configured to deactivate a pathogen deposited by the person on a surface adjacent the at least one disinfectant lamp 102. In another example, the person may cough or otherwise generate an airborne virus, and the lighting system 100 may be configured to deactivate the airborne virus before the airborne virus lands on a surface.

Many lamps have an expected and/or predicted lifespan (e.g., 3,000 hours of operation, 10,000 hours of operation, 20,000 hours of operation, 30,000 hours of operation, or 50,000 hours of operation). Often, disinfectant lamps are expensive and/or difficult to replace. Accordingly, it is often desirable to operate the lamp only when the lamp is needed. The effective range of disinfection lamps is often very limited, and the disinfection lamps may not need to be activated when the person is not in or near the effective range.

The lighting system 100 also includes at least one sensor 106. In some examples, the at least one disinfectant lamp 102 is activated in response to sensor feedback. Accordingly, the at least one disinfectant lamp 102 may turn on whenever the sensor is triggered, rather than (or in addition to) according to a predetermined schedule. In some examples, the at least one disinfectant lamp 102 remains deactivated unless the sensor is triggered and/or according to the predetermined schedule. For example, the at least one disinfectant lamp 102 may remain activated for a predetermined time (e.g., 5 seconds, 10 seconds, 50 seconds, 120 seconds, 20 minutes, or 10 hours) after the sensor trigger event and then deactivate unless the predetermined schedule directs the lamp to be on or another sensor trigger event has happened.

The at least one disinfectant lamp 102 may also turn on when other lamps (disinfectant lamps or other types of lamps) in the facility remain off. For example, each disinfectant lamp 102 or subgroup of disinfectant lamps 102 may response to signals from its own sensor. In some examples, at least one first disinfectant lamp 102 is activated in response to sensor feedback from a first sensor 106 and at least one other second disinfectant lamp 102 is activated in response to sensor feedback from a second sensor 106 and is unresponsive to feedback from the first sensor 106.

The at least one sensor 106 is operable to detect a person (i.e., a human). For example, the at least one sensor 106 may be a motion sensor or a passive infrared sensor. In some examples, the at least one sensor 106 is operable to detect a human when the human is within an activation range of the at least one sensor. The activation range may be a range surrounding and/or adjacent the at least one disinfectant lamp 102 and/or the lighting system 100.

In some examples, the activation range includes an effective range of the UVC light generated by the at least one disinfectant lamp 102 (the effective range may be, e.g., less than 20 meters, less than 15 meters, less than 10 meters, less than 5 meters, or less than 3 meters from the at least one disinfectant lamp 102) and/or an effective radiation zone that the at least one disinfectant lamp 102 can effectively irradiate. In some examples, far-UVC (200 nm to 230 nm) efficiently inactivates airborne aerosolized viruses with a very low dose of 2 $mJ/cm^2$ of 222 nm light (e.g., inactivating >95% of aerosolized H1N1 influenza virus). For example, for the SafeGlo2221.5FT by GMY Lighting Technology Co., Ltd. the effective range would be a volume of 50 square meters surrounding the lamp. In some examples, the lighting system 100 may be configured to turn on the at least one disinfectant lamp 102 if a person is in the effective range.

In some examples, the activation range includes the effective range and a supplementary range extending out from the effective range (e.g., extending out by between 1 and 20 meters, between 1 and 10 meters, or between 1 and 5 meters). Adding the supplementary range may allow the at least one disinfectant lamp 102 to begin generating radiation before the person reaches the effective range. The at least one disinfectant lamp 102 may need time (e.g., between 1 and 20 seconds, between 1 and 10 seconds or between 1 and 5 seconds) to turn on properly and start generating a desired level of flux. The at least one disinfectant lamp 102 may need time (e.g., between 1 and 20 seconds, between 1 and 10 seconds or between 1 and 5 seconds) to disinfect air and/or surfaces that the person will shortly be breathing in and/or touching.

Alternatively, or in addition, the activation range may be or include a region removed from the at least one disinfectant lamp 102 (e.g., more than 20 meters, more than 10 meters, or more than 5 meters away from the at least one disinfectant lamp 102). For example, the at least one disinfectant lamp 102 may be in a hallway, and the activation range may be a portion of the hallway that is more than 20 meters away so that the at least one disinfectant lamp 102 may turn on to be prepared to irradiate around a person who is coming down the hall.

As mentioned above, many lamps have an expected and/or predicted lifespan and are expensive and/or difficult to replace. Accordingly, it is often desirable to avoid replacing a lamp while a significant portion of the expected and/or predicted lifespan remains (e.g., more than 2 percent, more than 5 percent, more than 10 percent, or more than 25 percent).

In some examples, such as the illustrated example of FIG. 1, the lighting system 100 includes an automated tracking system 108 to automatically track usage of the at least one disinfectant lamp 102. In some examples, the tracking system 108 is operable to track how long the at least one disinfectant lamp 102 has been activated (i.e., the to-date usage of the at least one disinfectant lamp 102). Keeping track of how much of the lifespan remains is difficult when a lamp is not operating according to a predetermined or easily-tracked schedule. Keeping track of how much of the lifespan remains is particularly difficult when a plurality of lamps in a facility (e.g., a store or warehouse) are not all turned on or off at the same time and/or in a predicable way (e.g., one lamp in a facility turns on in response to a sensor signal while others remain off).

The tracking system 108 may allow the lighting system 100 to provide information to a user regarding the remaining lifespan of the at least one disinfectant lamp 102. Such information may help a user decide when to replace a lamp (e.g., rather than replacing all lamps in a facility at the same time even if some have a significant portion of their lifespan remaining). Alternatively, or in addition, such information may help a user to replace a lamp when it may be expected to stop working shortly, rather than waiting until the lamp dies before replacing it. Particularly when a lamp generates non-visible radiation, a user may not immediately replace a lamp when the lamp dies (e.g., due to not realizing that it has died or not being motivated to replace it immediately). This may lead to a period in which the benefits of the lamp are not realized. Information regarding lamp usage may allow lamp replacement events to be better planned.

In some examples, the tracking system 108 has total to-date usage information and is operable to generate remaining expected usage information. In some examples, the tracking system 108 can be adjusted (e.g., reset, reprogrammed for a different lifespan, and/or paused. For example, the user may replace the at least one disinfectant lamp 102, and may then reset the tracking system and/or update the expected lifespan so that the remaining expected usage information counts down from a different initial lifespan. The tracking system 108 may include one or more toggle (e.g., a depressible button and/or a soft button on a screen) for use in resetting, pausing, or reprogramming the tracking system.

The tracking system 108 and/or the sensor 106 may be coupled to the at least one disinfectant light 102 (e.g., so that they are in close proximity and/or in a single package). For example, the tracking system 108 and/or the sensor 106 may be supported by a luminaire 110 that includes the at least one disinfectant light 102.

In some examples, the lighting system 100 is configured to irradiate a space. For example, the lighting system 100 may be used to irradiate a space in a room of a building. In some examples, the lighting system 100 is configured to be mounted to a ceiling, wall, and/or floor of the room (i.e., the luminaire 110 is mounted to the surface) with the at least one disinfectant lamp 102 arranged to irradiate the space in the room when activated. For example, the lighting system 100 may be mounted to a ceiling of a hallway with the disinfectant lamp 102 arranged to irradiate downward into the hallway when activated.

Figure 2:
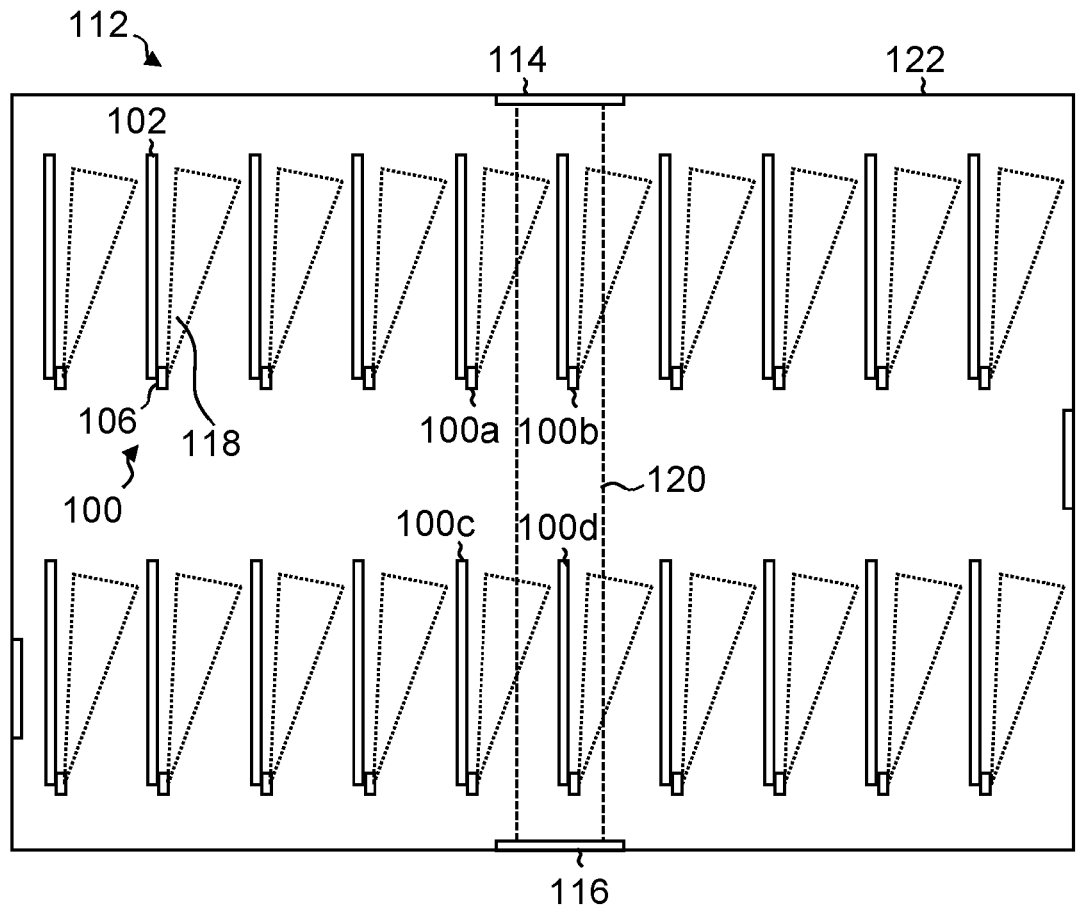
FIG. 2 is a schematic diagram of a first example of a facility illumination system.

Referring now to FIG. 2, in some examples, as in the illustrated example, the lighting system 100 is part of a facility illumination system 112 comprising multiple lighting systems 100. As illustrated, the at least one disinfectant lamp 102 of one lighting system 100 may be activated for a very different amount of time than another at least one disinfectant lamp 102 of another lighting system 100.

For example, if a person walks from a first door 114 to a second door 116 they will walk through the activation regions 118 of a first lighting system 100a, a second lighting system 100b, a third lighting system 100c, and a fourth lighting system 100d. If people walk from the first door 114 to the second door 116 along path 120 more than elsewhere in the room 122, then the at least one disinfectant lamp 102 of each of the first lighting system 100a, the second lighting system 100b, the third lighting system 100c, and the fourth lighting system 100d will be activated more than the at least one disinfectant lamp 102 of the other lighting systems. Accordingly, these disinfectant lamps 102 will need to be replaced earlier.

Figure 3:
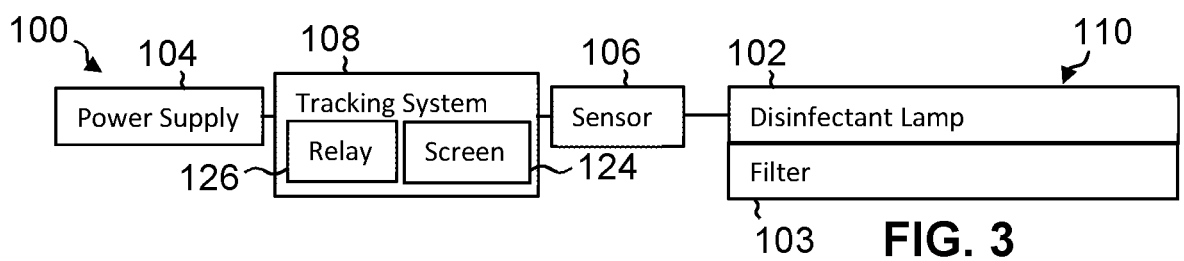
FIG. 3 is schematic diagram of a second example of a lighting system.

Referring now to FIG. 3, in some examples, as in the illustrated example the tracking system 108 includes at least one output device (e.g., at least one screen 124 and/or at least one wireless transmission device such as at least one wireless relay 126) and is operable to provide information via the at least one output device.

The tracking system 108 may include the at least one screen 124 to allow a user to gather information about the lamp when inspecting the luminaire 110. The tracking system 108 may also, or alternatively, include a wireless transmission device to facilitate sending information to at least one remote device (e.g., a smartphone or a remote server, such as via the Internet though a wireless router set up elsewhere in the facility). A wireless transmission device may allow a user to gather the information without visiting the luminaire 110. The at least one wireless relay 126 may be a Wi-Fi™ relay or a Bluetooth™ relay. While the tracking system 108 may send information continuously and/or in response to requests, in some examples the tracking system 108 is operable to send information periodically.

Figure 4:
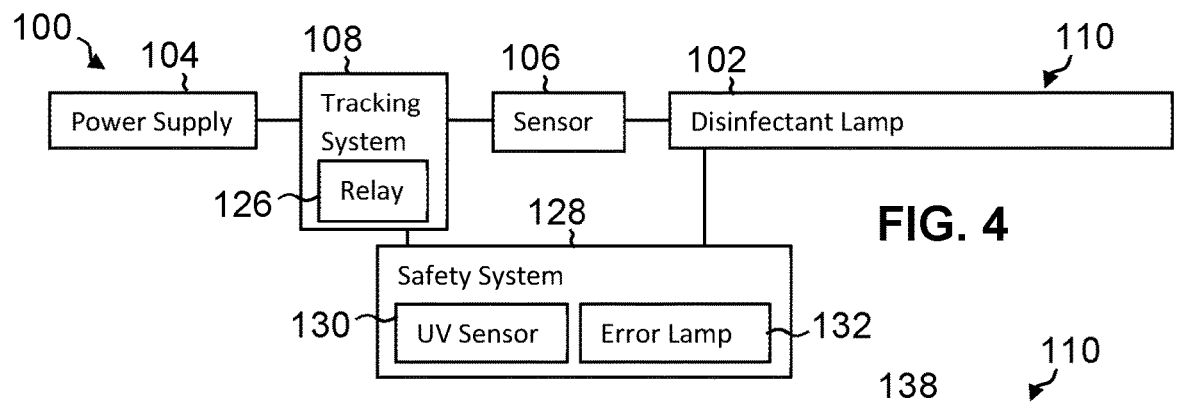
FIG. 4 is schematic diagram of a third example of a lighting system.

As in the illustrated example of FIG. 3, the tracking system 108 may include more than one type of output device (i.e., rather than only one, as in the example of FIG. 4). For example, the tracking system 108 may be mounted to the luminaire 110 and may display the remaining expected usage information on the at least one screen 124 and send the information via the at least one wireless relay 126 to the at least one remote device.

In some examples, the at least one disinfectant lamp 102 includes a filter 103. The filter 103 may be arranged to narrow the wavelength emitted. For example, the filter 103 may narrow the wavelength emitted to 200 nm to 230 nm, to 221 nm to 223 nm, or to about 222 nm.

Referring now to FIG. 4, in some examples, as in the illustrated example, the lighting system 100 includes a safety system 128 to automatically deactivate the at least one disinfectant lamp 102 in some circumstances. Some wavelengths of UVC light are highly dangerous to humans, and if the at least one disinfectant lamp 102 malfunctions and generates dangerous radiation the at least one disinfectant lamp 102 needs to be deactivated.

The safety system 128 includes a UV sensor 130 and is operable to shut off the at least one disinfectant lamp 102 if the UV sensor detects that the at least one disinfectant lamp 102 is emitting light outside of a predetermined safe range. In some examples, the predetermined safe range is 200 nm to 230 nm.

In some examples, the safety system 128 includes an error lamp 132. The error lamp 132 is activated to visually indicate an error if the UV sensor 130 detects that the at least one disinfectant lamp 102 is emitting light outside of the predetermined safe range. The error lamp 132 may be supported by the luminaire 110 and/or mounted in a remote control room to attract the attention of the user to indicate that the at least one disinfectant lamp 102 has malfunctioned and been deactivated. For example, the error lamp 132 may be a small light emitting diode configured to emit red visible light when activated, and may produce a pulsing red light to visually indicate the error.

In some examples, the safety system 128 is operable to send a notice to the at least one remote device if the UV sensor 130 detects that the at least one disinfectant lamp 102 is emitting light outside of the predetermined safe range.

Figure 5:
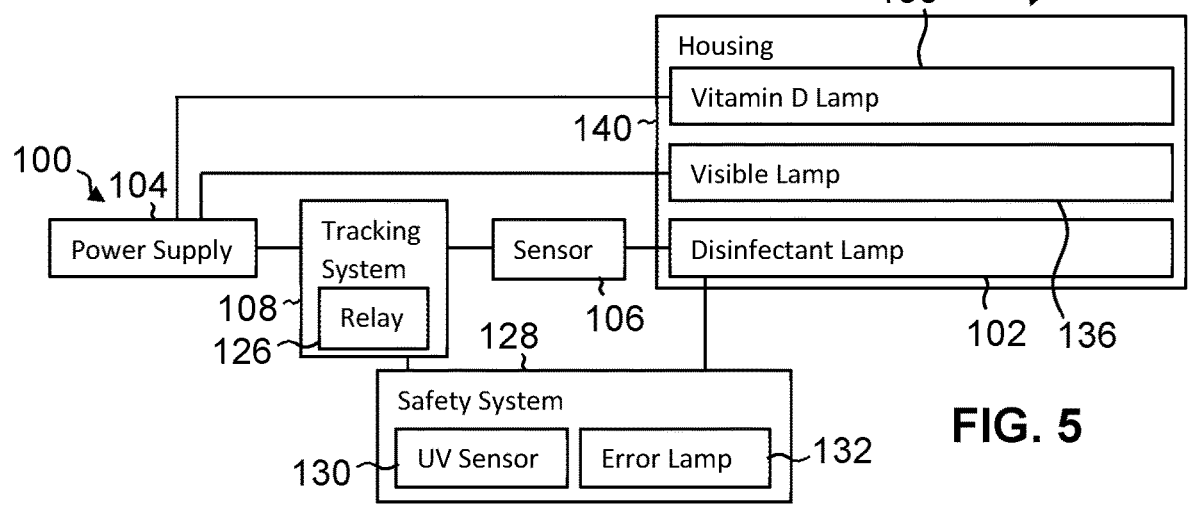
FIG. 5 is schematic diagram of a fourth example of a lighting system.

Referring now to FIG. 5, in some examples, as in the illustrated example, the luminaire 110 includes more than one type of lamp. All of the lamps of the luminaire 110 may be arranged to radiate in generally the same direction. For example, this may allow visible light and UVC light (or, e.g., visible light and UVC light and UVB light) to be directed through to same space, such as through the air around a person.

Activation and deactivation of the different types of lamps may be controlled the same way or differently. For example, the luminaire 110 may include a first type of lamp that is activated in response to sensors and a second type of lamp that is activated as soon as the luminaire 110 is powered on (i.e., without requiring sensor feedback).

In some examples, as in the illustrated example, the luminaire includes the at least one disinfectant lamp 102 and at least one visible lamp 136. In some examples, the at least one visible lamp 136 is configured to generate, when activated, visible light (e.g., with a wavelength between 380 nm and 750 nm). For example, the at least one visible lamp 136 may be and/or include a fluorescent tube light bulb or an incandescent light bulb.

In some examples, the at least one visible lamp 136 is configured to be activated as soon as the luminaire 110 is powered on (e.g., as soon as the luminaire 110 is plugged in and/or switched from an off state to an on state). The at least one disinfectant lamp 102 is configured to be activated in response to sensors, as discussed above, when the luminaire 110 is powered on. In some examples, the at least one visible lamp 136 is also configured to be activated in response to sensors (e.g., the sensor 106 or one or more other sensor).

In some examples, the luminaire 110 includes at least one vitamin D lamp 138. The at least one vitamin D lamp 138 is configured to generate, when activated, UVB light for the promotion of the production of vitamin D in the person (e.g., light having a wavelength between 270 nm and 330 nm).

In some examples, the at least one vitamin D lamp 138 is configured to be activated as soon as the luminaire 110 is powered on, however in some examples the at least one vitamin D lamp 138 is configured to be activated in response to sensors (i.e., like the disinfectant lamp). In some examples, the at least one vitamin D lamp 138 is configured to be intermittently energized when activated.

Accordingly, in some examples, the luminaire 110 includes a first lamp for general lighting, the first lamp operable to generate visible light when activated; a second lamp for disinfection, the second lamp operable to generate UVC light having a peak wavelength between 200 nm and 230 nm when activated; and a third lamp for causing vitamin D production, the third lamp operable to generate UV light having a peak wavelength between 270 nm and 300 nm when activated.

Figure 6:
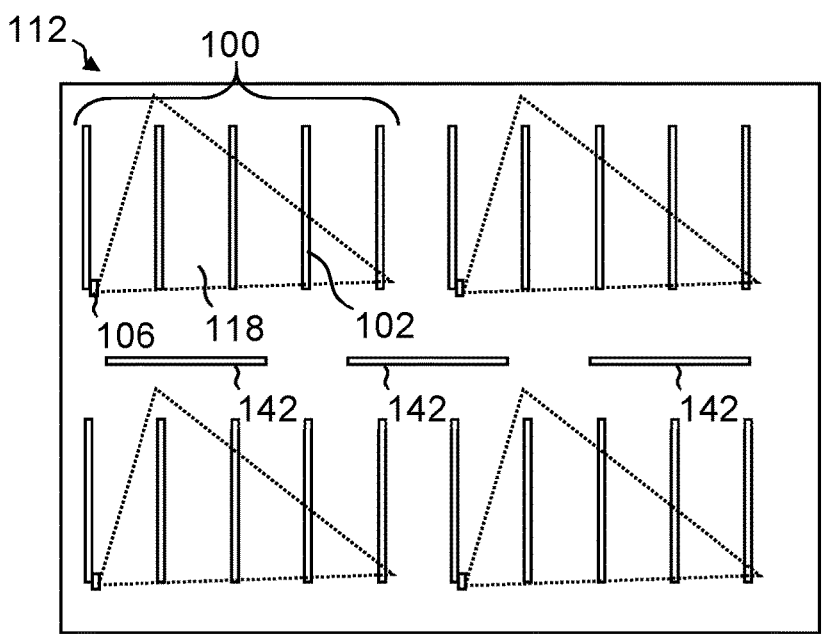
FIG. 6 is a schematic diagram of a second example of a facility illumination system.

Referring now to FIG. 6, in addition, or in alternative, to multiple lamps in one luminaire 110 and/or housing 140, the lighting system 100 may include multiple lamps separated from one another, in some examples. The facility illumination system 112 may also comprise one or more lamps 142 (e.g., visible lamps or other lamps) that are not part of one of the lighting systems 100.

Figure 7:
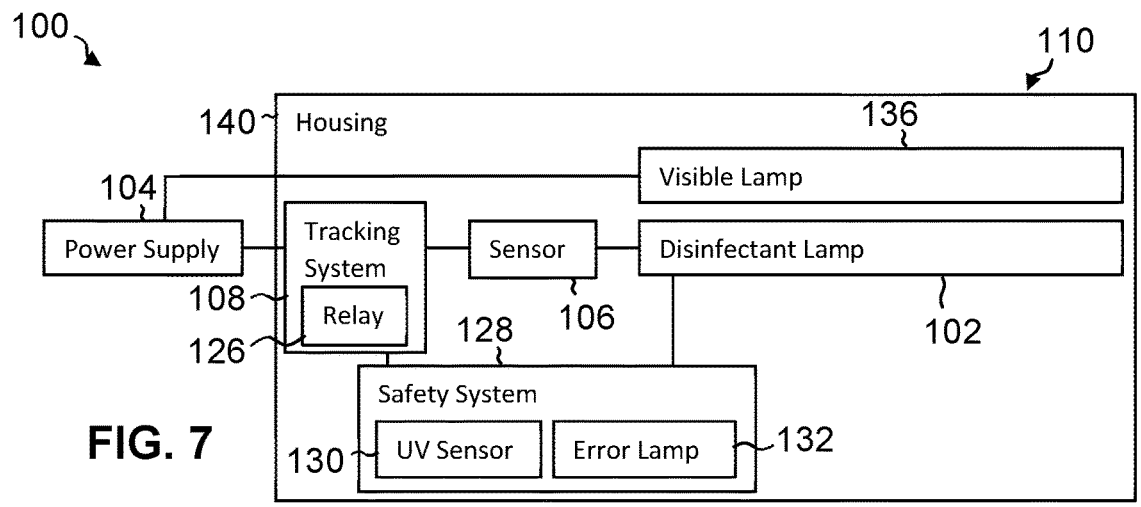
FIG. 7 is schematic diagram of a fifth example of a lighting system.
Figure 8:
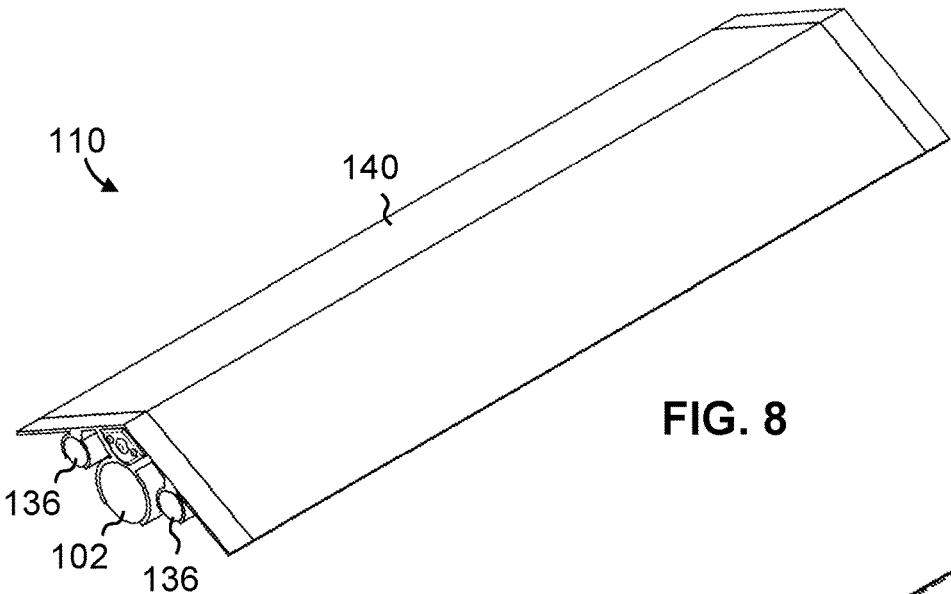
FIG. 8 is a top perspective view of a first example of a luminaire.
Figure 9:
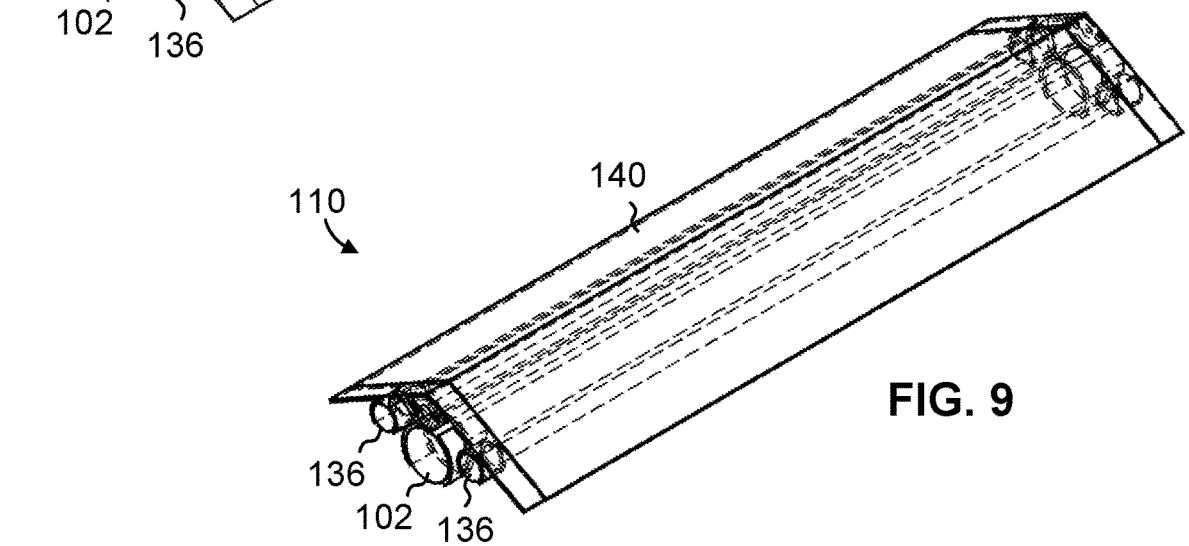
FIG. 9 is a transparent top perspective view of the first example of the luminaire of FIG. 8.
Figure 10:
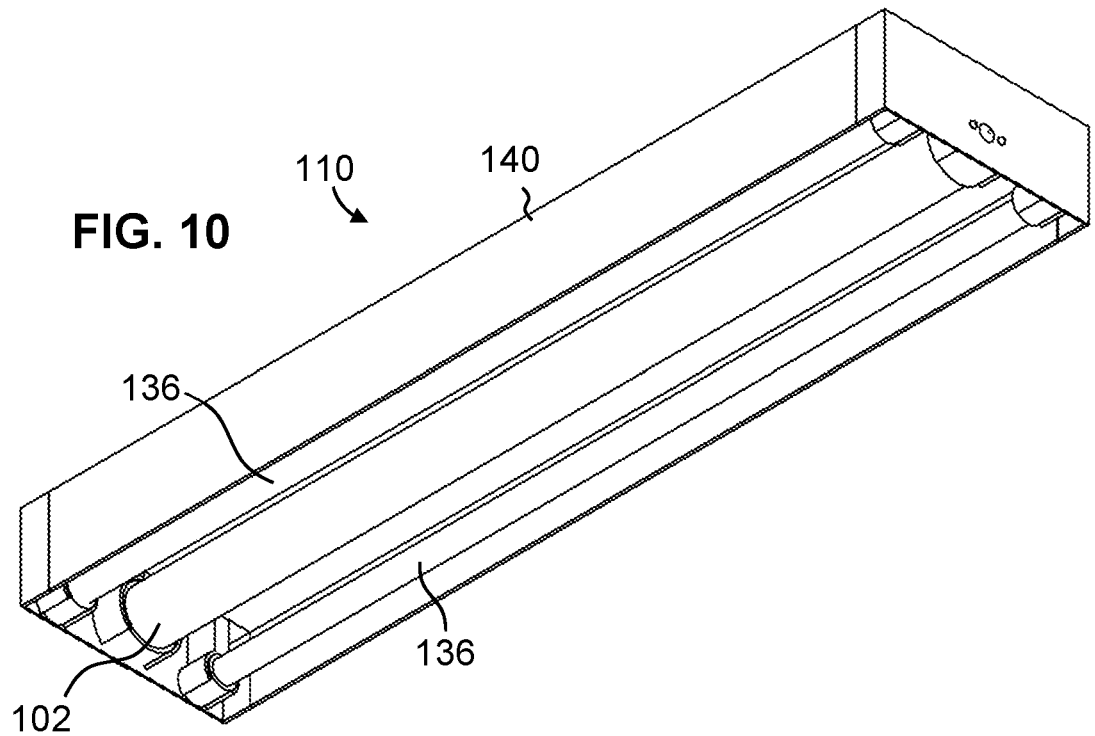
FIG. 10 is a bottom perspective view of a second example of a luminaire.
Figure 11:
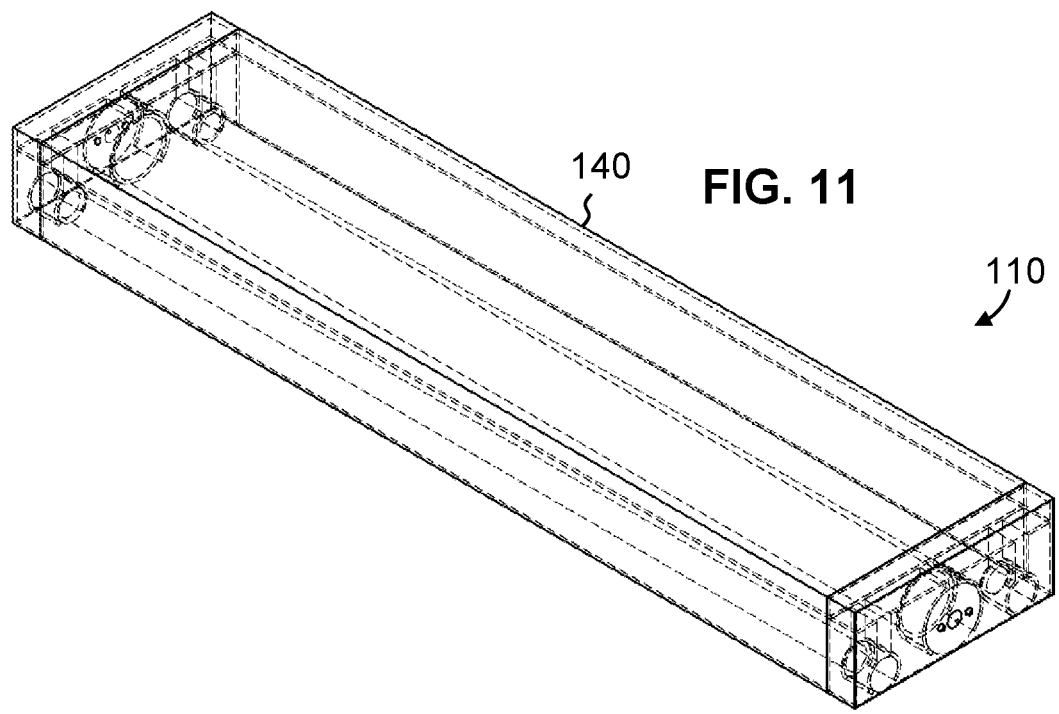
FIG. 11 is a transparent top perspective view of the second example of the luminaire of FIG. 10; and, FIG. 12 is a flow chart of a method.

Referring again to FIG. 5, as in the illustrated example, components of the lighting system 100, such as the sensor 106 and tracking system 108, may be remote from the luminaire 110 and/or the housing 140 of the luminaire 110. Alternatively, as indicated in FIG. 7, components of the lighting system 100 may be mounted to the luminaire 110, such as inside the housing 140. For example, the sensor 106, tracking system 108, and safety system 128, may be mounted to the luminaire 110, with a power supply 104 (e.g., a power cord) extending from the housing 140 of the luminaire 110.

Referring now to FIGS. 8 to 11, the luminaire 110 may come in a variety of different shapes and forms. As in the illustrated examples of FIGS. 8 to 11, the at least one visible lamp 136 may be a set of two lamps, each operable to generate visible light when activated, and the at least one disinfectant lamp 102 may be a single lamp. Accordingly, the luminaire 110 may include at least three lamps. As depicted, each of the lamps may be arranged to radiate in the same direction. In the illustrated examples, the three lamps include one disinfectant lamp 102 and two visible lamps 136. This may allow for a balanced output.

Figure 12:
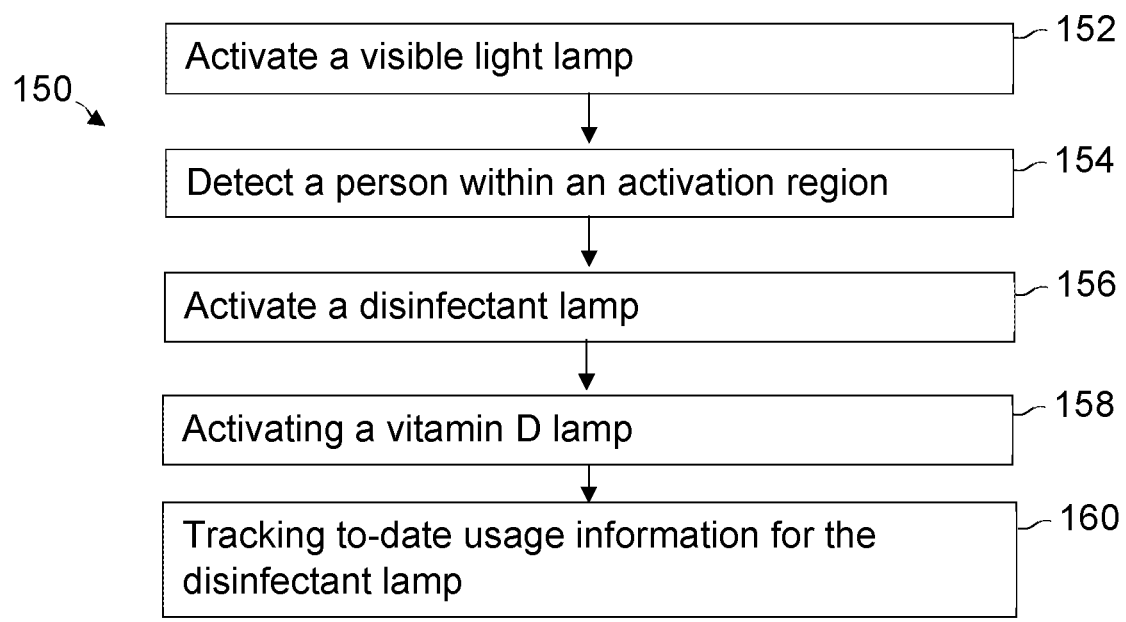

Referring now to FIG. 12, illustrated is a method 150 of operating a luminaire. The method 150 includes, at step 152, providing power to the luminaire 110 from a power supply 104 to activate a first lamp (e.g., the visible lamp 136) of the luminaire 110, the first lamp generating visible light.

The method 150 also includes, at step 154, after providing power to the luminaire (step 152), detecting a person within the activation region 118 adjacent the luminaire 110. The method 150 includes, at step 156, activating, in response to step 154, a second lamp of the luminaire, the second lamp (e.g., the disinfectant lamp 102) generating UVC light having a peak wavelength between 200 nm and 225 nm. In some examples, the method 150 also includes, at step 158, activating, in response to step 154, a third lamp (e.g., the vitamin D lamp 138) generating UV light having a peak wavelength between 270 nm and 300 nm The method 150 includes, at step 160, tracking to-date usage information, the to-date usage information indicating a total amount of time the second lamp has been activated so far.

The present invention has been described here by way of example only. Various modification and variations may be made to these exemplary embodiments without departing from the scope of the invention, which is limited only by the appended claims.

The invention claimed is:

1. A lighting system, comprising:
   a. a sensor operable to detect a person;
   b. a luminaire, including:
      i. a first lamp operable to generate visible light when activated, and
      ii. a second lamp operable to generate UVC light having a peak wavelength between 200 nm and 225 nm when activated, and
      iii. wherein the second lamp is communicatively coupled to the sensor and configured to be activated in response to the sensor detecting the person;
   c. a tracking system operable to track how long the second lamp has been activated and generate to-date usage information, the to-date usage information indicating a total amount of time the second lamp has been activated so far.

2. The lighting system of claim 1, wherein the sensor is operable to detect the person when the person is within an activation range of the second lamp, and the second lamp is configured to be activated in response to the sensor detecting the person when the person is within the activation range.

3. The lighting system of claim 2, wherein the activation range is an effective range of the UVC light of the second lamp, and the peak wavelength of the UVC light generated by the second lamp when the second lamp is activated is between 221 nm and 223 nm.

4. The lighting system of claim 2, wherein the second lamp is configured to remain activated for a predetermined activation time after the sensor detects the person when the person is within the activation range, and the second lamp is configured to deactivate after the predetermined activation time.

5. The lighting system of claim 4, wherein the sensor is supported by the luminaire.

6. The lighting system of claim 5, wherein the first lamp is configured to be activated when the luminaire is powered by a power source, and the second lamp is configured to be deactivated until both the luminaire is powered by the power source and the sensor detects the person when the person is within the activation range.

7. The lighting system of claim 6, wherein the first lamp is also configured to be deactivated until both the luminaire is powered by the power source and the sensor detects the person when the person is within the activation range.

8. The lighting system of claim 6, wherein the first lamp is configured to remain activated as long as the luminaire is powered by the power source regardless of whether the sensor detects the person when the person is within the activation range.

9. The lighting system of claim 6, wherein the tracking system is further operable to send the to-date usage information to a remote device.

10. The lighting system of claim 9, wherein the tracking system is configured to send the to-date usage information periodically.

11. The lighting system of claim 9, wherein the tracking system includes a wireless relay configured to transmit the to-date usage information to a remote device.

12. The lighting system of claim 11, wherein wireless relay is a Wi-Fi™ relay or a Bluetooth™ relay.

13. The lighting system of claim 12, wherein the remote device is at least one server.

14. The lighting system of claim 1, wherein the first lamp is a set of two lamps each operable to generate visible light when activated.

15. The lighting system of claim 1, further comprising a safety system including a UV sensor and operable to shut off the second lamp if the UV sensor detects that the second lamp is emitting light outside of a predetermined safe range.

16. The lighting system of claim 15, wherein the predetermined safe range is 200 nm to 230 nm.

17. A method of operating a luminaire, comprising:
   a. providing power to the luminaire from a power source to activate a first lamp of the luminaire, the first lamp generating visible light;
   b. detecting, after (a), a person within an activation region adjacent the luminaire; and
   c. activating, in response to (b), a previously-deactivated second lamp of the luminaire, the second lamp generating UVC light having a peak wavelength between 200 nm and 230 nm.

18. The method of claim 17, further comprising, following (c), tracking to-date usage information, the to-date usage information indicating a total amount of time the second lamp has been activated so far.

19. The method of claim 17, further comprising activating, in response to (b) a third lamp of the luminaire, the third lamp generating UV light having a peak wavelength between 270 nm and 300 nm.

20. A luminaire, comprising:
a. a first lamp for general lighting, the first lamp operable to generate visible light when activated;
b. a second lamp for disinfection, the second lamp operable to generate UVC light having a peak wavelength between 200 nm and 230 nm when activated; and
c. a third lamp for causing vitamin D production, the third lamp operable to generate UV light having a peak wavelength between 270 nm and 300 nm when activated.

* * * * *